United States Patent

Kording

[11] Patent Number: 5,677,036
[45] Date of Patent: Oct. 14, 1997

[54] MEDICAL PAD

[75] Inventor: Gerhard Kording, Burgwedel, Germany

[73] Assignee: Thamert Orthopadische Hilfsmittel GmbH & Co., KG, Burgwedel, Germany

[21] Appl. No.: 540,968

[22] Filed: Oct. 11, 1995

[51] Int. Cl.$^6$ .................. B32B 3/28; A61F 13/15
[52] U.S. Cl. ............ 428/156; 428/172; 428/167; 604/385.1
[58] Field of Search .................. 428/167, 156, 428/178, 172, 120, 137, 138, 155; 604/385.1

[56] References Cited

U.S. PATENT DOCUMENTS 4,435,178  3/1984  Fitzgerald .................. 604/365
4,676,786  6/1987  Nishino ..................... 604/378
4,758,240  7/1988  Glassman ................... 604/379

*Primary Examiner*—Donald Loney
*Attorney, Agent, or Firm*—Longacre & White

[57] ABSTRACT

A medical pad to support in as compression-free a manner as possible limbs and extremities and developed beyond the state of the art—wherein small nubs of the same material as the pad are present in mutually symmetrical rows, and, when the limbs and extremities to be supported come to rest on them will be deformed by them—is improved to avert the drawbacks of the known design. For that purpose, the invention provides support elements (replacing the hubs) which are configured in such manner that with maximal surface elasticity and thereby least loading of the limbs and extremities to be supported, the pad shall exert only slight compression on the said limbs and extremities.

10 Claims, 1 Drawing Sheet

MEDICAL PAD

BACKGROUND OF THE INVENTION a) Filed of the Invention

The invention concerns a cushioned medical pad to support limbs and extremities in as compression-free a manner as possible, developed beyond the state of the art wherein hubs of the same material as the pad are arrayed in mutually symmetrical rows on the pad surface and are deformed when the limbs or extremities to be supported come to rest against said pad.

b) Description of Related Art

The known design for cushioned medical pads entails the drawback that its nubs or projections evince a visible circular cross-section resulting in comparatively small cylindrical bodies, in other words, when pressure is applied to a specified area, these nub-like bodies experience compressions that locally may be very high.

SUMMARY OF THE INVENTION

Accordingly, it is the object of the present invention to create such a medical pad precluding the drawbacks of the state of the art and providing that in lieu of hubs, the support elements be configured in such manner that with maximally high surface elasticity, and hence, least load on the limbs or extremities to be supported, the pad shall only exert minor compression on them and furthermore over the entire area.

Square cross-sections of the support elements of the invention were found to be especially advantageous, and contrary to known designs, it is especially simple to manufacture in particular cushion-type support-element areas, merely slots being present between the individual squares to subdivide the pad surface, leaving in place a base joining the individual support elements to one another. The support elements being manufacturable using knives, saws or the like, the incisions dividing the surface of the pad may be made very narrow. Consequently high effectiveness is achieved with simultaneous considerable saving in material.

The configuration of the invention permits the application of different loads, namely a vertical compression from above on the cross-sections of the support elements, whereby the individual support elements are compressed downward and move laterally out of the way, whereby bellied, barrel-shaped elements are created of which the elasticity then drops rapidly and substantially as the compression increases.

The other variation is a lateral thrust on the support elements, so that friction takes place between the surface comprising the support elements and the rest surface functionally outfitting the pad. This friction may be positively stimulating on the supported extremity.

DETAILED DESCRIPTION OF THE PREFERRED EMBODIMENT

Figure 1:
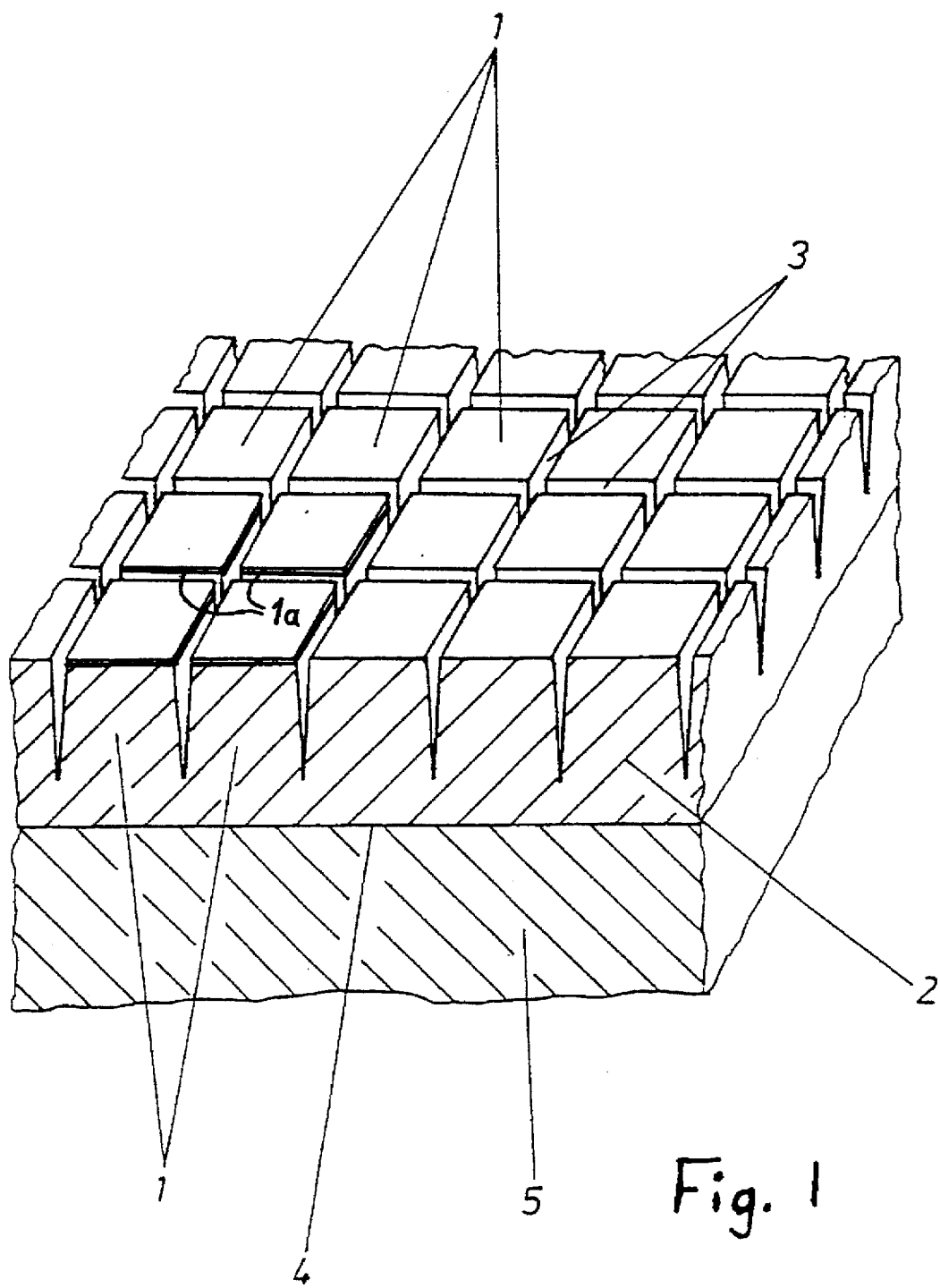
FIG. 1 is a perspective of a portion of a medical pad of the invention comprising support elements.

The FIGURE shows support elements 1 with square cross-sections, i.e. top views, which were manufactured by transverse and longitudinal incisions 3 in a layer 2 and extending downward like ravines but stopping short of the base 4 of the layer 2, whereby a continuous bottom layer such as a base remains underneath said ravines or incisions 3. All of the layer 2 may be made of an elastic material.

A further support layer 5 may be present underneath the layer 2 as shown in the FIGURE. Additionally or alternatively, a rest surface or a rest layer 1a may be deposited on the free square surfaces of the support elements 1 (see rest layer 1a deposited on four adjacent support elements in FIG. 1).

As a rule, the medical pad of the invention shown in cutaway form in FIG. 1 is placed against the limbs or extremities by that side toward which the free square surfaces of the support elements 1 are pointing. The pad need not evince corresponding support elements in all its portions. Instead, these support elements may be restricted to specified zones. Moreover, the support-element cross-sections are not mandatorily square. Rectangular cross-sections or other large cross-sections also are conceivable.

While the invention has been shown and described with reference to the embodiment of FIG. 1, it will be understood by those having skill in the art that various changes in form and detail may be made therein without departing from the spirit and scope of the invention.

I claim:

1. A cushioned medical pressure pad to support limbs and extremities in as compression-free a manner as possible, comprising:

a plurality of support elements projecting from and integrally formed with a base member, said support elements evincing a polygonal perimeter and separated by a plurality of incisions which are arranged in a plurality of rows and columns to thereby form a grid-like pattern on one side of said base member, wherein said support elements are configured in such manner that while evincing maximal surface elasticity and thereby least loading of the limbs and extremities to be supported, the pressure pad exerts only a slight compression over the entire surface of the limbs and extremities.

2. Pad defined in claim 1, wherein the support elements evince a square cross-section.

3. Pad defined in claim 1, wherein the incisions are narrow compared with the cross sectional areas of each of the support elements.

4. A cushioned medical pressure pad to support limbs and extremities with minimal compression, said medical pressure pad comprising:

a base portion forming a substrate of said medical pressure pad;

a plurality of support elements projecting from said base portion, said support elements evincing a polygonal cross-section, wherein the support elements are separated by slots which pass partially into and terminate within said base portion, said slots traverse said medical pad in a plurality of mutually symmetric rows and columns to form a grid-like pattern defining said polygonal cross-section.

5. The cushioned medical pad of claim 4, wherein said plurality of support elements are aligned adjacent to said slots to thereby define said mutually symmetric rows and columns.

6. The cushioned medical pad of claim 4, further comprising a secondary support layer affixed to said base portion at a position opposite to said plurality of support elements.

7. The cushioned medical pad of claim 1, wherein each of said incisions define a spaces between adjacent support elements, wherein said space gradually diminishes in width as said space progresses into said base member to thereby define a V-shaped incision.

8. The cushioned medical pad of claim 4, wherein each of said slots define a spaces between adjacent support elements, wherein said space gradually diminishes in width toward said base portion to thereby define a V-shaped incision.

9. The cushioned medical pad of claim 1, wherein said support elements are configured in such a manner that during use the support elements are compressed downward and move laterally outwards, whereby bellied, barrel-shaped elements are created of which the elasticity drops rapidly as compression is increased.

10. The cushioned medical pad of claim 4, wherein said support elements are configured in such a manner that during use the support elements are compressed downward and move laterally outwards, whereby bellied, barrel-shaped elements are created of which the elasticity drops rapidly as compression is increased.

* * * * *